United States Patent [19]
Wierzbicki et al.

[11] Patent Number: 4,939,164
[45] Date of Patent: Jul. 3, 1990

[54] STRONTIUM SALT

[75] Inventors: Michel Wierzbicki, Puteaux; Jacqueline Bonnet, Paris; Yannis Tsouderos, La Celle St-Cloud, all of France

[73] Assignee: Adir Et Compagnie, Neuilly-sur-Seine, France

[21] Appl. No.: 368,593

[22] Filed: Jun. 20, 1989

[30] Foreign Application Priority Data

Jun. 29, 1988 [FR] France ............... 88 08729

[51] Int. Cl.$^5$ ............... C07D 207/416; A61K 31/405
[52] U.S. Cl. ............... 514/423; 548/532

[58] Field of Search ............ 548/402, 532; 514/184, 514/423

[56] References Cited

U.S. PATENT DOCUMENTS 2,954,384  9/1960  Tatsuoka et al. ............ 548/532

Primary Examiner—Joseph Paul Brust
Assistant Examiner—Mary Sue Howard
Attorney, Agent, or Firm—Gordon W. Hueschen

[57] ABSTRACT

New distrontium salt of 3-(1-carboxymethyl-2-carboxypyrrol-4-yl)-pentanedioic acid which can be used therapeutically especially in the treatment of osseous diseases.

5 Claims, No Drawings

STRONTIUM SALT

The present relates to a new strontium salt, a process for the preparation thereof and pharmaceutical compositions containing it.

It relates especially to the distrontium salt of 3-(1-carboxymethyl-2-carboxypyrrol-4-yl)-pentanedioic acid of the formula I

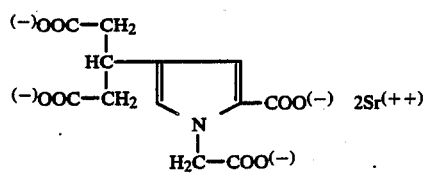

The present invention also relates to a process for the preparation of the distrontium salt of the formula I, characterised in that:

the thieno[2,3-b]pyrrole compound of the formula II.

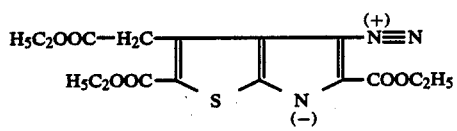

is dediazotised to obtain a compound of the formula III:

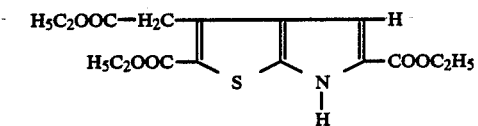

which is treated with ethyl bromoacetate in the presence of sodium in anhydrous ethanol to obtain the compound of the formula IV:

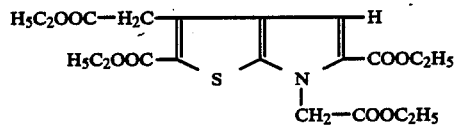

which is reacted with Raney nickel in an anhydrous ethanol medium to obtain the compound of the formula V:

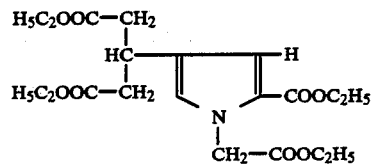

which is heated under reflux in the presence of sodium hydroxide in aqueous alcoholic medium to give the acid of the formula VI:

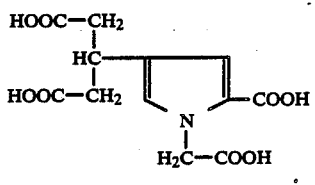

which is reacted with $Sr(OH)_2$ in aqueous medium to obtain the corresponding distrontium salt.

The thieno[2,3-b]pyrrole derivative (II) used as starting material is described in Bull. Soc. Chim. (1975) pages 1786–1792.

The 3-(1-carboxymethyl-2-carboxypyrrol-4-yl)-pentanedioic acid of the formula VI is a new product which can be used as a starting material in the chemical and pharmaceutical industry, especially in the synthesis of the distrontium salt of the formula I. As such, it is therefore included in the present invention.

The distrontium salt of the formula I possesses valuable pharmacological and therapeutic properties, especially remarkable anti-osteoporosis properties, which therefore permit its use as a medicament especially in the treatment of osseous diseases.

It is known from the prior art that some strontium salts can be used therapeutically. In particular, GB Patent No. 2,091,998 claims the use of strontium salts with customary organic acids in the treatment of urinary lithiasis. Some publications in the literature, especially Gastineau, Proc. Staff. Meetings Mayo Clinic 35, 105–111 (1960); Skoryna, Can. Med Assoc. 125 (7), 702–712 (1981), Skoryna, Trace Subst. Environ Health 18, 3–23 (1984), mention the activity of strontium lactate, gluconate and carbonate in the treatment of osteoporosis.

The distrontium salt of the present invention, in addition to being novel compared with the previously known strontium salts, has surprising advantages over the latter, especially a better bioavailability, as demonstrated in the pharmacological study described hereinafter, which makes it possible to administer lower chemical doses when treating osteoporosis.

The present invention also relates to pharmaceutical compositions containing as active ingredient the strontium salt of the formula I, mixed or associated with a suitable pharmaceutical excipient, such as, for example, distilled water, glucose, lactose, starch, talc, ethylcellulose, magnesium stearate or cocoa butter.

The pharmaceutical compositions so obtained are generally presented in dosage form and may contain from 200 to 300 mg of active ingredient. They may be in the form of tablets, dragees, soft gelatin capsules, drinkable solutions, injectable solutions or suppositories, and may, depending on the particular case, be administered orally, rectally or parenterally at a dose of from 200 to 300 mg from 2 to 4 times per day.

The following Examples illustrate the invention.

EXAMPLE 1

Synthesis of the distrontium salt of 3-(1-carboxymethyl-2-carboxypyrrol-4-yl)-pentanedioic acid

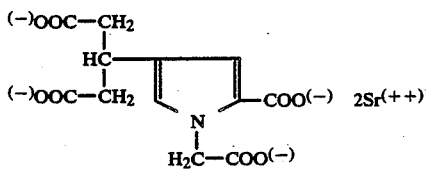

The synthesis comprises the following preparative stages:

(a) 3-ethoxycarbonylmethyl-4-diazo-2,5-diethoxycarbonylthieno[2,3-b]pyrrole, {prepared according to Bull. Soc. Chim. (1975) pages 1786–1792, from 425 g (1.03 moles) of 6-acetyl-4-amino-3-ethoxycarbonylmethyl-2,5-diethoxycarbonylthieno[2,3-b]pyrrole} to which a few milliliters of N $H_2SO_4$ have been added, is refluxed in 5 liters of ethanol under a stream of nitrogen. The acetaldehyde formed is distilled off and a small amount of ethanol is passed through in order to concentrate the medium. The reaction is continued until all of the diazo group has disappeared (readily demonstrated by its intense yellow colour—deposit on silica). The whole is concentrated in 2 liters of aqueous ethanol, the product is caused to crystallise, filtered and washed twice with 200 ml of an ethanol/water mixture (½) each time. There are finally obtained 256 g of 3-ethoxycarbonylmethyl-2,5-diethylcarbonylthieno[2,3-b]pyrrole which is substantially pure and melts at 147°–148° C. (Yield: 70%).

(b) The 256 g (0.72 mole) of 3-ethoxycarbonylmethyl-2,5-diethoxycarbonylthieno[2,3-b]pyrrole obtained above are dissolved at ambient temperature in a solution of sodium ethoxide prepared by dissolving 33 g (1.43 equivalents) of sodium in 3 liters of anhydrous ethanol. 240 g (1.44 mole) of ethyl bromoacetate are added in a single addition and the reaction mixture is heated under reflux for 3 hours. The precipitate formed is filtered off and the filtrate is concentrated to approximately 1.2 liters. Filtration is carried out to isolate the new precipitate obtained and the two precipitates are combined and washed with approximately 1 liter of distilled water and then with 500 ml of petroleum ether. 269 g of pure 3,6-diethoxycarbonylmethyl-2,5-diethoxycarbonyl-thieno[2,3-b]pyrrole are thus obtained, m.p.: 190° C. (Yield: 85%).

(c) The 269 g of product so obtained are dissolved in 8 liters of ethanol, while warming if necessary. 1600 cm³ of Raney nickel are added thereto and the whole is heated under reflux for one hour. The ethanol is then filtered while still warm and then evaporated. 252 g of substantially pure 4-(1,3-diethoxycarbonylprop-2-yl)-2-ethoxycarbonyl-1-ethoxycarbonylmethylpyrrole are finally obtained. B.p./0.02 mm=190° C. (Yield 100%).

(d) 643 ml of 4N sodium hydroxide (2.57 moles), 210 ml of distilled water and 210 ml of ethanol are added to those 252 g of product (0.61 mole). The whole is heated while stirring and reflux is maintained for 1 hour 30 minutes. The ethanol is then evaporated and exactly 2.57 moles of HCl are added. Filtration is then carried out and the precipitate obtained is dried.

The dry precipitate is taken up in 5 liters of acetone containing approximately 5% water. The insoluble portion (sodium chloride) is filtered off and the acetone is evaporated. The evaporation residue is dissolved in 20 liters of distilled water and passed over 3.4 kg of sulphonic resin Dowex HCR WE. The solution is evaporated to dryness using a Sihi pump and without heating. 148 g of substantially pure 3-(1-carboxymethyl-2-carboxypyrrol-4-yl)-pentanedioic acid are obtained in the form of a pink product which melts at 130° C. (Yield: 81%).

(e) 262.9 g (0.9892 mole) of $Sr(OH)_2.8H_2O$ and 5.8 liters of distilled water are added to the 148 g (0.4946 mole) of acid so obtained. After dissolving at ambient temperature and filtering off the slight cloudiness, the filtrate is evaporated using a Sihi pump and the product obtained is washed with 300 ml of anhydrous diethyl ether. 232 g of the distrontium salt of 3-(1-carboxymethyl-2-carboxypyrrol-4-yl)pentanedioic acid are obtained, a sample of which is recrystallised from water in the form of the defined hexahydrate, $C_{12}H_9NO_8Sr_2.6H_2O$ (UV: λmax: 265 mm, ε: 8500).

EXAMPLE 2

Pharmacological study (1) Experimental osteoporosis on immobilised rats

This study showed that the distrontium salt of 3-(1-carboxymethyl-2-carboxypyrrol-4-yl)-pentanedioic acid administered daily at a dose of 940 mg/kg per os to rats subjected to local immobilisation of one rear paw reduces the loss of osseous material observed among the controls. This is evidenced in a clear and significant manner with regard to the osseous mineral contents, without any significant change in the other osseous or serous parameters.

(2) Bioavailability tests on rats. These tests related to:

The absolute bioavailability and the relative bioavailability by studying the serous kinetics of strontium after the oral administration to rats of the distrontium salt of 3-(1-carboxymethyl-2-carboxypyrrol-4-yl)-pentanedioic acid and comparison strontium salts, i.e. strontium chloride and strontium gluconate. After a single oral administration of 67 mg/kg of the distrontium salt of 3-(1-carboxymethyl-2-carboxypyrrol-4-yl)-pentanedioic acid, the strontium is absorbed with an absolute bioavailability of 51%, with maximum concentration being achieved in less than one hour. The strontium therefore passes rapidly and in a substantial quantity to the serous level.

The bioavailability of strontium appears to be comparable in the case of the distrontium salt of 3-(1-carboxymethyl-2-carboxypyrrol-4-yl)-pentanedioic acid and strontium chloride, and a little greater in the case of the gluconate if the comparison is made at equivalent doses with respect to the amount of elemental strontium.

However, at equal doses of active ingredient, the distrontium salt of 3-(1-carboxymethyl-2-carboxypyrrol-4-yl)-pentanedioic acid, like strontium chloride, by providing a greater mass of strontium than does the gluconate, permits absorption of a greater amount of strontium, and therefore better efficacy.

We claim:

1. The distrontium salt of 3-(1-carboxymethyl-2-carboxypyrrol-4-yl)-pentanedioic acid of the formula I:

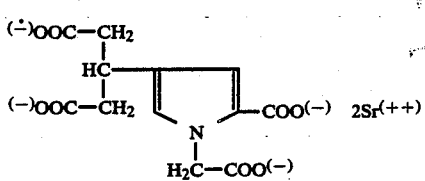

2. 3-(1-carboxymethyl-2-carboxypyrrol-4-yl)-pentanedioic acid.

3. Process for the preparation of the distrontium salt of claim 1, characterised in that the thieno[2,3-b]pyrrole compound of the formula II:

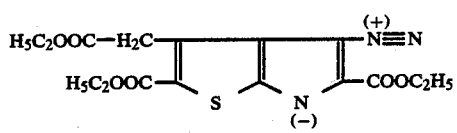

is dediazotised to obtain a compound of the formula III:

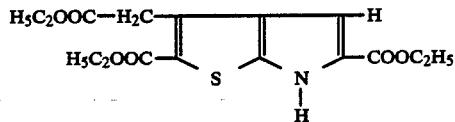

which is treated with ethyl bromoacetate in the presence of sodium in anhydrous ethanol to obtain the compound of the formula IV:

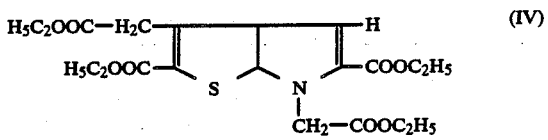

which is reacted with Raney nickel in an anhydrous ethanol medium to obtain the compound of the formula V:

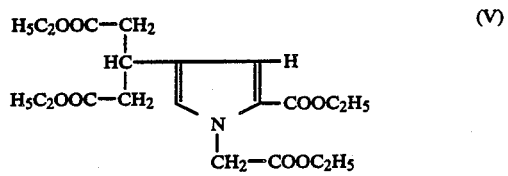

which is heated under reflux in the presence of sodium hydroxide in aqueous alcoholic medium to give an acid of the formula VI:

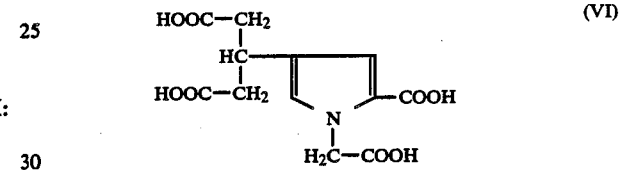

which is reacted with Sr(OH)$_2$ in aqueous medium to obtain the corresponding distrontium salt.

4. Pharmaceutical compositions containing, as active ingredient, the distrontium salt of 3-(1-carboxymethyl-2-carboxypyrrol-4-yl)-pentanedioic acid, with suitable pharmaceutical excipients.

5. A method for treating a living animal body afflicted with osseous diseases, comprising the step of administering to the said living animal an amount of the compound of claim 1 which is effective for the alleviation of the said condition.

* * * * *

UNITED STATES PATENT AND TRADEMARK OFFICE
CERTIFICATE OF CORRECTION

PATENT NO. : 4,939,164

DATED : July 3, 1990

INVENTOR(S) : Michel Wierzbicki, Jacqueline Bonnet, Yannis Tsouderos

It is certified that error appears in the above-identified patent and that said Letters Patent is hereby corrected as shown below:

Column 1, line 4; "present relates" should read
-- present invention relates --.

Column 3, line 58; "210." should read -- 210 --.

Column 4, line 17; "4-yl)pentanedioic" should read
-- 4-yl)-pentanedioic --.

Signed and Sealed this

Eighth Day of October, 1991

Attest:

HARRY F. MANBECK, JR.

Attesting Officer     Commissioner of Patents and Trademarks